(12) United States Patent
Perricone

(10) Patent No.: US 6,365,623 B1
(45) Date of Patent: Apr. 2, 2002

(54) TREATMENT OF ACNE USING LIPOIC ACID

(76) Inventor: Nicholas V. Perricone, 27 Coginchaug Ct., Guilford, CT (US) 06437

(*) Notice: Subject to any disclaimer, the term of this patent is extended or adjusted under 35 U.S.C. 154(b) by 0 days.

(21) Appl. No.: 09/475,514

(22) Filed: Dec. 30, 1999

Related U.S. Application Data

(63) Continuation-in-part of application No. 09/415,792, filed on Oct. 8, 1999, which is a continuation-in-part of application No. 08/971,820, filed on Nov. 17, 1997, now Pat. No. 5,965,618.

(51) Int. Cl.⁷ .............. A61K 31/38; A61K 31/355; A61K 31/045; A61K 31/07
(52) U.S. Cl. .............. 514/448; 514/724; 514/725; 514/458
(58) Field of Search .................. 514/724, 725, 514/458, 448

(56) References Cited

U.S. PATENT DOCUMENTS

| | | | |
|---|---|---|---|
| 5,472,698 A | 12/1995 | Rawlings et al. | 424/401 |
| 5,569,670 A | 10/1996 | Weischer et al. | 514/440 |
| 5,583,156 A | * 12/1996 | Yu et al | 514/473 |
| 5,641,475 A | * 6/1997 | Yu et al. | 424/65 |
| 5,646,190 A | * 7/1997 | Martin | 514/724 |
| 5,665,364 A | * 9/1997 | McAtee et al. | 424/401 |
| 5,693,664 A | 12/1997 | Wessel et al. | 514/440 |
| 5,709,868 A | 1/1998 | Perricone | 424/401 |
| 5,728,735 A | 3/1998 | Ulrich et al. | 514/560 |
| 5,965,618 A | 10/1999 | Perricone | 514/558 |

FOREIGN PATENT DOCUMENTS

| | | | | |
|---|---|---|---|---|
| EP | WO 95/05852 | * | 3/1995 | A61K/45/06 |
| JP | 63008315 | | 1/1988 | |

OTHER PUBLICATIONS

Chandraratna et al, 123CA:132781, 1995.*
Brogden, R.N., and Goa, K.L., Drugs 63: 1–12 (1997).
Downie, M.T., and Kealey, T., J. Invest. Derm. 111: 199–205 (1998).
Haramaki, N., et al., Free Rad. Biol. Med., 22: 535–542 (1997).
Ibbotson, S.H., J. Invest. Derm., 112: 933–938 (1999).
Packer, L., et al., Free Rad. Biol. Med. 19: 227–250 (1995).
Physicians' Desk Reference 2000, 54th ed., 502–503, 1104–1105, 2139–2142.
Sen, C.K., et al., Free Rad. Biol. Med., 25: 89 (1998).

* cited by examiner

Primary Examiner—Russell Travers
(74) Attorney, Agent, or Firm—Mary M. Krinsky

(57) ABSTRACT

Active acne and acneiform scars are treated by topical application of a composition containing lipoic acid and/or a lipoic acid derivative such as dihydrolipoic acid, a lipoic or dihydrolipoic acid ester, a lipoic or dihydrolipoic acid amide, a lipoic or dihydrolipoic acid salt, and mixtures of any of these to reduce erythema, pore size, and scarring. Topical application of lipoic acid and/or a lipoic acid derivatives are advantageously used with at least one adjunct ingredient such as a retinoid, an antibiotic, or benzoyl peroxide conventionally used for acne, alone or in combination with dimethylaminoalcohol, an α-hydroxy acid such as glycolic acid, a tyrosine, tocotrienol, and/or a fatty acid ester of ascorbic acid. One preferred embodiment contains a combination of lipoic acid, an α-hydroxy acid, and dimethylaminoalcohol.

12 Claims, No Drawings

TREATMENT OF ACNE USING LIPOIC ACID

CROSS-REFERENCES TO RELATED APPLICATIONS

This application is a continuation-in-part of U.S. application Ser. No. 09/415,792, filed Oct. 8, 1999, which was a continuation-in-part of U.S. application Ser. No. 08/971,820, filed Nov. 17, 1997, which issued on Oct. 12, 1999 as U.S. Pat. No. 5,965,618, both of which are incorporated herein by reference.

STATEMENT REGARDING FEDERALLY SPONSORED RESEARCH

Not Applicable

BACKGROUND OF THE INVENTION

1. Field of the Invention

This invention relates primarily to methods and compositions for the treatment of acne *vulgaris*. Acne is the most common pustular condition of the skin, disfiguring afflicted persons with inflammatory and noninflammatory lesions (including pustules, papules and comedones) during the active phase, and with atrophic scars afterwards. It occurs most commonly in teenagers, but is not confined to adolescents, as increasing numbers of persons aged >20 years are seeking advice on treatment for acne (Brogden, R. N., and Goa, K. L., *Drugs*, 1997, 53: 511–519; this reference and others cited below are hereby incorporated herein in their entireties by reference). Although acne is generally considered to be self-limiting, its social effects can be substantial, and it may have its most severe effects on the psyche (ibid.). In about 60% of teenagers, disease severity is sufficient for them to self-medicate with proprietary preparations, or seek medical advice.

Acne is a multifactorial disease affecting the pilosebaceous units of the skin. Each unit consists of a large, multilobed sebaceous gland, a rudimentary hair and a wide follicular canal lined with stratefied squamous epithelium. They are found over most of the body surface but are largest and most numerous on the face, chest, and upper back. Normally, desquamated follicular cells are carried to the surface by the flow of sebum. Under the abnormal circumstances of acne *vulgaris*, an abnormal desquamation process provokes increased sloughing of the epithelium, which becomes more cohesive because of defective keratinization. This process causes blockage of the follicular orifice with accumulation of dead cells. Androgen stimulates the undifferentiated hormonally responsive cells making up the outer layer of the sebaceous gland lobule to divide and differentiate. Sebum production favors proliferation of the anaerobe Propionibacterium acnes, which is a normal commensal to the pilosebaceous unit, which can elicit hypersensitivity responses in acne.

The basic lesion of acne is the microcomedo. Accumulation of sebum and keratinous debris results in a visible closed comedo, or whitehead, and its continued distension causes an open comedo, or blackhead. The dark color of blackheads is due to oxidized melanin. Blackheads and microcysts are noninflammatory lesions of acne, but some comedones evolve into inflammatory papules, pustules, or nodules, and can become chronic granulomatous lesions. The initial inflammatory cell in an acute acne papule is the CD4+T lumphocyte. Duct rupture is not a prerequisite for inflammation, which is due to the release of pro-inflammatory substances from the duct. When inflammation develops, neutrophil chemotaxis occurs. These neutrophils secrete hydrolytic enzymes that cause further damage and increased permeability of the follicular wall. In pustules, neutrophils are present much earlier. More persistent lesions exhibit granulomatous histology that can lead to scarring.

The aims of treating acne are to prevent scarring, limit disease duration, and reduce the social and psychological stress that affects many patients, particularly teenagers. Conventional treatment is directed at correcting the three major factors that seem to cause acne: (1) androgenic stimulation of the sebaceous glands and increased sebum production; (2) abnormal keratinization and impaction in the pilosebaceous canal causing obstruction to sebum flow; and (3) proliferation of P. acnes. Thus, topical agents that remove comedones, such as topical retinoids are particularly effective because they normalize desquamation within the follicular orifice, which allows the sebum to flow freely onto the surface of the skin; adalpalene, tretinoin, and tazarotene have been shown to have efficacy in treating mild to moderate acne, but all three have reported to have skin-irritating side effects including erythema, pruritis, burning/stinging, and scaling/flaking (*Physicians' Desk Reference®*, 54th ed. 2000, pp 502–503, 1104–1105, and 2139–2142, hereinafter referred to as "PDR"). Topical vitamin A preparations and benzoyl peroxide have been used to treat acne for some time. However, it has been recently reported that benzoyl peroxide seems to induce free radical production that can produce skin changes that qualitatively resemble ultraviolet B damage, e.g., increases in epidermal thickness, and deleterious changes in elastin and glycosaminoglycan content (Ibbotson, S. H., et al., *J. Inves. Derm.*, 1999, 112: 933–938). Topical and oral antibiotics (especially tetracycline, erythromycin, and clindamycin) are sometimes prescribed for patients with inflammatory papules and pustules; but, in addition to the undesirability antibiotic overuse in general, disadvantages to such treatments include phototoxicity and interactions with other medications. Other factors that play a role in exacerbating acne, including oil-based cosmetics and some drugs (e.g., androgenic hormones, high-progestin birth control pills, systemic corticosteroids, and iodide- and bromide-containing agents) are often minimized during acne treatment.

Human sebum contains an unusual mixture of lipids, with the major lipid classes being triacylglycerides (TAG, conventional fat, ≈40 to 60%), wax esters (≈19 to 26%), and squalene (≈11 to 15%), but at least 15 different neutral and polar lipids have been identified in human sebaceous glad tissue (Downie, M. M. T., and Kealey, T., *J. Invest. Derm.*, 1998, 111: 199–205). Recent studies have shown that people with acne have abnormal sebum secretions in that the ratios of essential fatty acids in sebaceous triacylglycerides (TAG, conventional fat) are skewed, as are the proportions of TAG, squalene and wax esters. It has been hypothesized that the viscosity and irritant level of these substances contribute to sebum obstruction and rupture of pilosebaceous units observed in acne. Lipogenesis in human sebaceous glands varies depending upon the metabolic state of the cells, glandular fluctuations, and the presence or absence of different substrates or other substances effecting competition between sterol and TAG pathways (Downie and Kealey, cited above). It would be desirable to utilize this biochemical information to devise alternate treatments for acne.

It would also be desirable to not only treat acne *vulgaris* manifested by the symptoms of pustule, papule, and comedone formation described above, but also minimize scar formation and treat atrophic acneiform scars left after resolution of the active phase. Scars result from the formation of granulation tissue and matrix formation following inflammation. (For a review, see Sahl, W. J., and Clever, H., *Internat. J. Derm.*, 1994, 33: 681–691 (part I) and 763–769 (part II), and parent case U.S. Pat. No. 5,965,618 to Perricone cited above). Atrophic scars of the face left after acne have been traditionally treated with invasive methods such as scar revision, laser ablation, and chemical peels. Non-invasive techniques have consisted of topical application of tretinoin, as well as the application of estrogens and α-hydroxy acids. None of these non-invasive procedures have been effective enough to justify widespread use as a therapy.

2. Description of Related Art

Lipoic acid was originally identified as a bacterial growth factor present in the water-soluble fraction of liver and yeast. It was found to be necessary for the oxidative decarboxylation of pyruvic acid by *Streptococcus fecalis* and for the growth of *Tetrahymena gelii*, and replaced acetate for the growth of *Lactobacillus casei*. Subsequent research showed that lipoic acid was a growth factor for many bacteria and protozoa, and it served as a prosthetic group, coenzyme, or substrate in plants, microorganisms, and animal tissues, participating in a variety of metabolic processes including acyl transfer reactions unction determined that it is a co-factor for α-keto-dehydrogenase complexes. Its reduced form, dihydrolipoic acid (herein sometimes referred to as DHLA), is a potent sulfhydryl reductant. In aqueous systems, both lipoic acid and DHLA exhibit antioxidant actions (reviewed by Packer, L., et al., *Free Rad. Biol. Med.*, 1995, 19: 227–250 (1995)). Lipoic acid has been shown to maintain microsomal protein thiols, protect against hemolysis, and protect against neurological disorders. The protective effect of dietary supplementation of lipoic acid against ischemia/reperfusion injury in the Langendorff isolated heart model has also been demonstrated lipoic acid has been suggested for treating systemically, or as adjuvant systemic medication for, liver cirrhosis, atheroscilerosis, diabetes, neurodegenerative diseases, heavy metal poisoning, mushroom poisoning and Chagas disease.

A couple of recent references have suggested that lipoic acid might be useful in dermatological compositions. In a 1988 Japanese patent publication (JP 63008315), lipoic acid in cosmetics at concentrations of 0.01% to 1%, preferably 0.05% to 0.5%, or in topical "quasi-drugs" at concentrations of 0.1% to 1.5%, preferably 0.5% to 1.0%, were suggested for inhibiting tyrosinase, and thus melanin formation, to whiten skin.

In 1995, Rawlings, et al., disclosed a composition and method for "improving or preventing the appearance of dry, flaky wrinkled, aged, photodamaged skin and treating skin disorders" (U.S. Pat. No. 5,472,698, column 2, lines 51 to 54) using a synergistic combination of serine and/or N-acetyl serine and a thiol, an "S-ester", and/or a disulfide (id., lines 28 to 33). Lipoic acid was mentioned as encompassed by the latter ingredient (column 3, lines 29 to 30), but the terminology in the patent was confusing because thiols and S-esters were disclosed as preferable over disulfides such as lipoic acid. And the focus of the patent was stimulation of sphingolipid synthesis in skin, with lipoic acid shown to be the same as control compositions, and have no effect in combinations without serine.

A year later, Weischer, et al., (in U.S. Pat. No. 5,569,670), pharmaceutical compositions containing a synergistic combination of α-lipoic acid and/or dihydrolipoic acid with specific enantiomers of these, together with some vitamins, including C and E (column 1, lines 3 to 15), were disclosed as useful, primarily for treating diabetes (see the claims). However, anti-inflammatories (abstract, line 8 and column 2 at line 16) as well as treatments for retroviruses and other pathological conditions were included, with an emphasis on veterinary applications (column 13, lines 42 to 62). In a test model for inflammation (observing rat edema), the R-enantiomer of lipoic acid was superior to lipoic alone or to vitamin E alone (column 3, lines 37 to 40). Suggested administration was oral, parenteral or intravenous (column 7, line 31 to end, et seq.), preferably oral (column 11, line 42), but application to skin and mucous membranes was mentioned (column 12, lines 58 to 60). An ointment was disclosed in Example 6; the others described suppositories, capsules, ampules, and tablets.

Similarly, U.S. Pat. No. 5,693,664 to Wessel, et al., from the same research group, was directed to diabetes treatments, particularly where insulin resistance is observed (column 1, lines 10 to 14 and the claims) by use of the R-enantiomer of α-lipoic acid. Again, one enantiomer, not a racemate, was employed (column 6, lines 18 to 19). Indeed, the S-enantiomer decreased the effect of insulin in an experimental study reported (column 3, lines 61 to 65). Suggested adminstration was primarily oral (column 6, lines 61 to 66), though parenteral and intravenous are mentioned (ibid., and column 3, lines 7 to 8).

U.S. Pat. No. 5,728,735 to Ulrich, et al., again from the same group, stressed use of an enantiomer (column 1, lines 28 to 54), particularly the R-enantiomer (see the claims), and not a racemate, for combatting pain and inflammation in a variety of conditions (id., lines 58 to 59; inflammations are listed in column 5, line 64 to column 6, lines 9 and include neurodermatitis and psoriasis). Suggested administrations were oral, intravenous, or infusions (column 3, lines 28 to 30, 51, 62 to 63 and 65), but solutions and emulsions for topical application were mentioned (column 6, lines 29 to 34 and 65 to 68, and column 8, lines 16 to 18). Only tablets and ampules were illustrated. All the reported findings of the group are complicated by the fact that the metabolic effects of the R- and S-enantiomers are now known to be different, as are the enzymes that process the enantiomers in cytosolic and mitrochondrial systems (Haramaki, N., et al., *Free Rad. Biol. Med.* 22: 535–542 (1997)). Moreover, different stereospecific reduction by intact cells and tissues has also been observed (ibid.).

More recently, Perricone suggested the use of lipoic acid in dermatological compositions for the treatment of skin damage, particularly inflammation and aging (U.S. Pat. No. 5,709,868), and also for the treatment of scars, particularly for hypertrophic and keloid scars (U.S. Pat. No. 5,965,618). As explained in those patents, the antioxidant activity of lipoic acid appears to prevent free radical damage to cells and cell components. Modulation of the activation of transcription factor AP-1 by lipoic acid may also affect the activity of matrix metaloproteinases, allowing collagen remodeling which is necessary for scar improvement.

Inflammation in skin is mediated by several active chemicals and metabolites of arachidonic acid. Arachidonic acid is oxidized by cyclo-oxygenase and lipoxygenase to active metabolites such as the leukotrienes and 5- and 12-hydroxyeicosatetraenoic acid (HETES). Within the arachidonic acid cascade, many free radicals are generated, which both perpetuate and magnify the inflammatory cascade, resulting in skin damage and manifested clinically as erythema. The redox state of the cell determines gene expression. Transcription factor nuclear factor kappa-B (NFκ-B) and others are affected by the redox state of the cell. When the cell undergoes oxidative stress, i.e., ultraviolet radiation, ionizing radiation, infection, and free radicals created by metabolism, the inhibitory fraction of NFκ-B is dissociated from the molecule. Once the inhibitory fraction is dissociated from the NFκ-B molecule, it then migrates to the nucleus of the cell, begins transcription, and inflammatory mediators, including cytokines, are produced. AP-1, a transcription factor, appears to be activated bimodally, i.e., both under oxidation and reduction, resulting in matrix remodeling.

BRIEF SUMMARY OF THE INVENTION

It is an objective of this invention to provide compositions and methods for the treatment of acne *vulgaris*, both during the active phase, and for acneiform scars afterwards, It is a corresponding objective to alleviate the negative social and psychological impacts frequently suffered by persons afflicted with acne. Facial lesions and scars are one of the strongest forces driving the cosmetic industry. It would be desirable to have new and improved methods for treating acne, as it is so widely observed in the population, particularly among teenagers who are especially sensitive about their appearance.

It is another and more specific objective of the invention to provide topical compositions and methods for acne lesion and acne scar treatment based upon the application of compositions containing lipoic acid and/or lipoic acid derivatives to skin areas disfigured by acne. Preferred embodiments further employ adjunct ingredients.

These and other objectives are accomplished by the present invention, which provides compositions and methods for the treatment of acne *vulgaris*, and improvements of currently employed therapies, which comprise topical application to skin areas exhibiting acne of an effective amount of lipoic acid, lipoic acid derivatives or mixtures thereof, typically in association with a dermatologically acceptable carrier. In most preferred embodiments, at least one other adjunct ingredient is included in the treatment or composition. Adjunct ingredients include, but are not limited to, α-hydroxy acids such as glycolic and/or lactic acid; tocotrienols; fatty acid esters of ascorbic acid such as ascorbyl palmitate; tyrosine; antibiotics such as erythromycin, clindamycin, or tetracycline; retinoids such as tretinoin, adapalene, or tazarotene; or methyl- or ethyl-aminoalcohols such as dimethylaminoethanol. Benzoyl peroxide is included in some compositions. Adjunct ingredients enhance the efficacy of the treatment, and minimize or eliminate skin irritation to perilesional areas. Use of compositions of the invention are additionally beneficial in minimizing the adverse effects of surgical acne procedures such as dermabrasion, laser ablation, scar revision, and chemical peels.

The amount of lipoic acid or derivative thereof (hereinafter referred to collectively as lipoic acid or "LA" for ease of reference) necessary to treat acne is not fixed per se, and necessarily is dependent upon the identity and form of lipoic acid employed, the amount and type of any adjunct ingredients employed, the user's skin type, and the severity and extent of the acne and/or acneiform scars. In some typical embodiments, the composition contains from about 0.1% to about 7 weight %, lipoic acid, more narrowly from about 0.25% to about 5 weight %. In one embodiment, about 2% to 5% lipoic acid is employed. The amount of adjunct ingredient or ingredient combination varies with what is employed, but typical concentration ranges vary from about 0.01% to about 10%, and in many cases from about 0.025% to about 7% by weight, depending upon the identity of the ingredient or ingredient combination.

DETAILED DESCRIPTION OF THE INVENTION

This invention is based upon the finding that lipoic acid and/or its derivatives are useful for the treatment of acne *vulgaris* in the active phase and for acneiform scars. It has been surprisingly found that lipoic acid applied to the faces of persons with acne not only reduces erythema and acneiform scars, but also reduces pore size, and the beneficial effects increase over time. Moreover, lipoic acid and/or its derivatives provide surprising benefits when used with currently employed acne medications as adjunct ingredients because skin irritant side effects are minimized or eliminated, and other adjunct ingredients not heretofore suggested as acne medications improve the overall beneficial effects of LA compositions.

As used herein, the term "acne" includes all types of acne in all stages, including acne *vulgaris* observed in adolescents, acne observed in endocrinologic conditions characterized by excess androgen secretion, and the like, in the active inflammatory (pustule-, papule-, comedone-forming) and noninflammatory (blackhead- and cyst-forming) phases, and post-inflammatory (healing, scarring, and scarred) phase. The term "lipoic acid" encompasses thioctic acid (1,2-dithiolane-3-pentanoic acid; 1,2-dithiolane-3-valeric acid), $C_8H_{14}O_2S_2$, formula weight 206.32, and its reduced form, dihydrolipoic acid. It has been variously known as acetate replacing factor, protogen A, and pyruvate oxidation factor. As mentioned above, for convenience, as used herein, where the properties and advantages of "lipoic acid" (or LA) are discussed as an active ingredient in the practice of the invention, both lipoic acid and its derivatives are encompassed. "Lipoic acid derivatives" include thioctic acid esters, particularly alkyl esters such as fatty acid esters, amides, particularly those isolated from or mimicking naturally occurring lipoamides, salts, particularly alkali metal salts, anhydrides and specifically includes the reduced form, dihydrolipoic acid and its esters, amides and salts. One particularly efficacious derivative that exhibits increased cellular uptake and biological activity useful in the practice of the invention is N,N-dimethyl,N-2-amidoethyl lipoate recently described by Sen, C. K., et al. (*Free Radical Biol. Med.*, 1998, 25: 89) and called lipoic acid plus (LA-Plus). Since lipoic acid is both fat- and water-soluble, it is an advantage of the invention that it can be used in either lipid or aqueous-based compositions, and it readily crosses cellular membranes and disperses in extracellular and intracellular tissue components. Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid.

As mentioned above, lipoic acid is fat-soluble. Therefore, lipoic acid preparations can be applied neat to skin tissue. It is an advantage of the invention that the active compound is fatty so that it physically contributes to the lubrication of affected skin areas to which it is applied.

However, only effective amounts of lipoic acid are needed to treat acne and acneiform scars, so generally topical application to exposed or affected skin sites is accomplished in association with a carrier, and particularly one in which the active ingredient is soluble per se or is effectively solubilized (e.g., as an emulsion or microemulsion). Where employed, the carrier is inert in the sense of not bringing about a deactivation of the lipoic acid or derivative, and in the sense of not bringing about any adverse effect on the skin areas to which it is applied.

Suitable carriers include water, alcohols, oils and the like, chosen for their ability to dissolve or disperse lipoic acid and any other ingredients used in the treatment. Generally, even low concentrations of active ingredients in a carrier are suitable, depending upon the application regimen and adjunct ingredients employed. Many embodiments contain from about 0.1% to about 7% by weight, more narrowly from about 0.25% to about 5% by weight, LA. Many embodiments contain more than 1 weight % lipoic acid and/or lipoic acid derivative, e.g., from about 1.1% to about 3 to 5 weight % LA. One efficacious embodiment contains from about 2% to about 5% by weight. Examples are illustrated hereafter.

While the carrier for lipoic acid can consist of a relatively simple solvent or dispersant, it is generally preferred that the carrier comprise a composition more conducive to topical application, and particularly one which will form a film or layer on the skin to which it is applied so as to localize the application and provide some resistance to perspiration and/or one which aids in percutaneous delivery and penetration of the active ingredients into lipid layers of the scarred area. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers. Most preferred for skin are those carriers which are fat-soluble, i.e., those which can effectively penetrate skin layers. And in embodiments employing lipoic acid with at least one other conventional acne medication or other adjunct ingredient, one or more of the active ingredients may be encapsulated to increase product shelf life and preserve maximal activity.

As has been mentioned, most preferred embodiments of this invention contain at least one other adjunct ingredient in addition to lipoic acid. Indeed, it is an advantage of the invention that some adjunct ingredients are conventional acne medications. Lipoic acid not only augments their effects, but minimizes or eliminates their side effects. Adjunct ingredients include, but are not limited to, not only retinoids, topical antibiotics, and benzoyl peroxide conventionally used in acne treatments, but also methyl-/ethyl-aminoalcohols, α-hydroxy acids, tyrosine tocotrienols, and fatty acid esters of ascorbic acid.

Retinoids useful as adjunct ingredients with LA include commercially available adapalene, tazarotene and/or tretinoin described by Brogden and Goa and the PDR cited above. Adapalene, for example, is currently sold as a gel or solution marketed as Differin®. Tretinoin can be obtained as a cream, gel or encapsulated microsphere marketed as Avita®, Renova®, or Retin-A®. Tazarotene is marketed as a Tazorac® gel. Effective formulations typically contain from about 0.025% to about 0.1% by weight retinoid or retinoid mixture with LA concentrations set out above. Lipoic acid compositions can either contain at least one retinoid, or be applied before, during, or after treatment with at least one retinoid. It is an advantage of the invention that use of lipoic acid in conjunction with a retinoid in treatments employing retinoids provides a method for treating acne using less retinoid than would be required if a retinoid is used alone, because topical application of retinoids results in skin irritation in some patients. As set out in the PDR sections cited above, even at recommended frequency and dose levels, typically up to about 10% of patients complain of inflammation, swelling, and burning sensations when using products containing retinoids (including control patients who have no acne), but acne patients tend to overuse the medications. Lipoic acid can reduce this amount and the duration of drug use in patients presenting acne conditions warranting the beneficial normalizing desquaminating properties that retinoids can provide, and alleviate side effects. Preferred compositions of the invention also minimize or eliminate skin irritation, particularly in areas surrounding acne lesions.

Lipoic acid may also be used in combination with topical or oral antibiotics such as tetracycline, clindamycin, and erythromycin sometimes used for acne cases, particularly for patients with inflammatory papules and pustules. Lipoic acid may be added to an antibiotic preparation, or applied before, during, or after antibiotic treatment. As with retinoid therapy, an advantage of using lipoic acid with antibiotics in cases where they might be efficacious is that a lower antibiotic dose or a shorter antibiotic regimen may be employed. It is now recognized that prevalent use of antibiotics in general is undesirable, and long-term use of antibiotics can cause nausea, gastrointestinal upset, phototoxicity, enhanced susceptibility to yeast infection, and interactions with other medications. Use of lipoic acid advantageously minimizes the amount of antibiotic necessary to cause improvement in patients presenting with an extreme inflammatory phase of acne.

Adjunct ingredients not previously suggested for acne are also efficacious as ingredients with LA in the practice of the invention. Among these are methyl- and ethyl- derivatized lower amino alcohols. These include methyl- and ethyl-amino alcohols such as dimethylaminoethanol, monomethylaminoethanol, diethylaminoethanol, monoethylaminoethanol, their propanol and butanol counterparts (all isomers of monomethylaminopropanol, dimethylaminopropanol, monoethylaminopropanol, diethylaminopropanol, monomethylaminobutanol, dimethylaminobutanol, monoethylaminobutanol, and diethanolaminobutanol), and derivatives acylated with organic acids, particularly the lower ($C_1$ to $C_3$) carboxylic acids such as acetic acid because these esters are less bulky, and others set out in U.S. Pat. No. 5,554,647 to Perricone such as para-chlorophenylacetic acid esters. Dimethylaminoethanol is used in one embodiment. Typical amounts of lower amino alcohols such as dimethylaminoethanol employed in LA compositions of the invention range from about 0.5% to about 5% by weight, more narrowly from about 2% to about 3% by weight.

In some embodiments α-hydroxy acids and/or their derivatives are included as adjunct ingredients. As used herein, the terminology "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those set out in parent case U.S. Pat. No. 5,965,618 at column 6 lines 4 to 29. In some preferred embodiments, glycolic and/or lactic acid or their derivatives are employed. Glycolic acid is especially efficacious. Preferred compositions contain effective amounts of α-hydroxy acids. Typcal concentrations range from about 1% to about 10% by weight, more narrowly from about 3% to about 7%, by weight α-hydroxy acid.

Tyrosine may be added as an adjunct ingredient to LA compositions of the invention in some embodiments. Typical concentrations range from about 0.05% to about 5%, more narrowly from about 1% to about 3%, by weight tyrosine. One particularly efficacious embodiment of the invention contains lipoic acid, glycolic or lactic acid, and dimethylaminoalcohol; another further contains tyrosine, Fat-soluble fatty acid esters of ascorbic acid (vitamin C) may be added to the lipoic acid composition for treating acne in some embodiments. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate.

Tocotrienol may also be added to lipoic acid compositions of the invention, alone or in combination with an ascorbyl esters and/or α-hydroxy acids or their derivatives in some embodiments. The term "tocotrienol" encompasses natural and/or synthetic counterparts of tocopherol (vitamin E) that bear unsaturated tails, and include, but not limited to, α-, β-, γ-, and δ-tocotrienols, tocotrienol P25, desmethyl-tocotrienol, didesmethyl-tocotrienol, their synthetic counterparts, their counterparts having methylated or demethylated chroman rings, tocotrienol-enriched fractions obtained from natural or synthetic sources, stabilized derivatives, and mixtures thereof, more fully described in parent case U.S. Pat. No. 5,965,618 at column 5, line 53 to column 7, line 23.

Any compositions of the invention employing LA as an active ingredient, alone or in combination with one or more adjunct ingredients, can also contain benzoyl peroxide, alone, or in combination with a vitamin A preparation conventionally used for acne treatments. One embodiment employs LA with tocotrienols and benzoyl peroxide. Lipoic acid can be applied together in the same composition with these other ingredients, or before, during, or after treatment with benzoyl peroxide and a tocotrienol. An advantage of using lipoic acid with benzoyl peroxide in any composition with or without one or more adjunct ingredients is that the deleterious skin damage caused by repeated administration of benzoyl peroxide reported by Ibbotson, et al., cited above is limited, as is perilesional skin irritation.

Lipoic acid can also be used advantageously as adjunct acne therapy before, during, or after surgical procedures for acne, such as dermabrasion, laser ablation, scar revision, and chemical peels typically used for extreme cases of acneiform scars. In this embodiment, it is especially efficacious in the post-physical treatment phases, as it helps heal the skin, prevent scarring, and may minimize the number and severity of the procedures to which scarred acne patients may be subjected.

While not wishing to be bound to any theory, it is possible that lipoic acid is efficacious in the treatment of acne because it is both fat- and water-soluble and readily disperses in cell membranes and other cellular components. Lipoic acid readily penetrates skin and is found in high concentrations in sebaceous gland tissue four hours after application. Because of its solubility, it is sometimes referred to as a universal antioxidant. It acts as a free radical scavenger and neutralizer, and prevents the cross-linking of cell membranes that is often seen in acne in its post-inflammatory phases. By the same token, LA modulation of free radicals and other oxidative species affects gene expression, including expression of nuclear factor κ-B (NF-κB), nitric oxide synthetase and other mediators at all stages of proinflammation and inflammation. Lipoic acid's alteration of lipid peroxidation, protein cross-linking, growth factor stimulation, and membrane permeability may explain its negative effect on the symptoms of acne.

Because of its activity within the pyruvate dyhydrogenase complex, lipoic acid has also been termed the metabolic antioxidant. Again, while not wishing to be bound to any theory, it may be that lipoic acid can boost energy production in sebaceous glands, which results in a more normal sebum production with triglycerides and lipids in normal ratios. Since lipogenesis in human sebaceous glands depends upon the metabolic status of the cells, the addition of lipoic acid by providing increased energy production would be therapeutic.

Generally in the practice of the method of the invention, the composition is topically applied to the affected skin areas in a predetermined or as-needed regimen either at intervals by application of a lotion or the like, it generally being the case that gradual improvements is noted with each successive application. Insofar as has been determined based upon clinical studies to date, no adverse side effects are encountered.

It is an adavantage of the invention that topical application of lipoic acid provides a simple, non-invasive, nontoxic, over-the-counter topical method for treating all phases of acne. Lipoic acid compositions decrease erythema observed with acne pustules, papules and whiteheads, and a marked decrease in lesion numbers. The effect is enhanced by use of adjunct ingredients such as dimethylaminoethanol, α-hydroxy acids, and/or tyrosine. Lipoic acid compositions decrease pore size, minimizing sebum accumulation and keratinous debris that cause both whiteheads and blackheads observed in acne. Lipoic acid minimizes scar formation, and provides marked losses of scar borders and decreases in scar depth where scars have already formed. Topically applied lipoic acid also seems to fill in scar tissue, making it more equal to adjacent normal skin. Moreover, compositions containing lipoic acid with adjunct ingredients such as retinoids, α-hydroxy acids, tyrosine, and/or dimethylaminoethanol, appear to successfully treat active acne lesions without harming surrounding skin tissue. And with these physical effects, persons using lipoic acid topical compositions experience a reducion in the social and psychological stress often associated with acne patients suffering facial disfigurements.

EXAMPLES

The following examples are presented to further illustrate and explain the present invention and should not be taken as limiting in any regard. Unless otherwise indicated, all percentages are by weight. Lipoic acid was supplied by the Henkel Corporation and was placed into a lecithin-based oil-in-water cream at a level of 5% for use by acne patients. This composition was used in the studies unless otherwise indicated.

Eight patients with acne *vulgaris* and/or acneiform scars were evaluated and photographed at the beginning of the study. The patients were asked to cleanse their faces with Cetaphil™ lotion twice daily, and then to apply the test lipoic acid composition. Clinical evaluations were made every four weeks thereafter. Photographs were retaken at the end of twelve weeks, and five patients continued treatment for up to a year.

The following parameters were reported in clinical assessments by a dermatologist in the follow-up evaluations:
1. visibly apparent changes in erythema
2. visibly apparent changes in pore size
3. visibly apparent changes in acneiform scars, evaluated on a three-point qualitative scale, with moderate improvement judged by marked loss of scar borders and decreases in scar depth, moderate to good improvement judged by loss of scar borders and a marked decrease in scar depth, and excellent improvement judged by complete loss of acneiform scar borders and filling equal to that of adjacent normal skin.

Within three to four weeks, there was a marked decrease in pustules, papules, and comedones. These benefits continued to increase over a period of three to four months. All patients with atrophic scars improved, with two patients with severe atrophic acne scars showing an improvement of 80%. The results may be summarized as follows:

|  | Scar Depth<br>% Improvement | Erythema<br>% Improvement | Pore Size<br>% Improvement |
| --- | --- | --- | --- |
| Pt. #1 | 80 | 80 | 50 |
| Pt. #2 | 50 | 80 | 90 |
| Pt. #3 | 50 | 50 | 90 |
| Pt. #4 | 70 | 50 | 50 |
| Pt. #5 | 50 | 50 | 90 |
| Pt. #6 | 80 | 50 | 90 |
| Pt. #7 | 70 | 50 | 90 |
| Pt. #8 | 50 | 80 | 50 |

The study was repeated using patients with acne *vulgaris* as test subjects who applied a composition containing 5% lipoic acid and 5% glycolic acid. Patients were evaluated every two weeks. In every patient, marked decreases in microcomedones, comedones, pustules, and erythema were observed after two weeks. These benefits continued to increase over a period of three to four weeks.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for reducing and preventing acneiform scars and reducing pore size comprising topically applying to affected skin areas a composition containing lipoic acid or a lipoic acid derivative in a dermatologically acceptable carrier.

2. A method according to claim 1 wherein the lipoic acid derivative is selected from the group consisting of dihydrolipoic acid, a lipoic or dihydrolipoic acid ester, a lipoic or dihydrolipoic acid amide, lipoic acid plus, a lipoic or dihydrolipoic acid salt, and mixtures thereof.

3. A method according to claim 1 wherein lipoic acid, dihydrolipoic acid, or mixtures thereof are applied.

4. A method according to claim 1 wherein the composition further contains an α-hydroxy acid ingredient, tyrosine, or mixtures thereof.

5. A method according to claim 4 wherein the α-hydroxy acid ingredient is selected from the group consisting of glycolic acid, lactic acid, and mixtures thereof.

6. A method according to claim 1 wherein the composition comprises from about 0.1% to about 7% lipoic acid or lipoic acid derivative.

7. A method according to claim 6 wherein the composition comprises from about 0.25% to about 5% lipoic acid or lipoic acid derivative.

8. A method according to claim 7 wherein the composition comprises from about 2% to about 5% lipoic acid or lipoic acid derivative.

9. A method according to claim 1 wherein the composition further comprises a tocotrienol selected from the group consisting of α-tocotrienol, β-tocotrienol, γ-tocotrienol, δ-tocotrienol, desmethyl-tocotrienol, didesmethyl-tocotrienol, tocotrienol-P25, and mixtures thereof.

10. A method according to claim 1 wherein the composition further comprises a fatty acid ester of ascorbic acid.

11. A method according to claim 1 wherein the composition further comprises a methyl- or ethyl-aminoalcohol ingredient selected from the group consisting of dimethylaminoethanol, monomethylaminoethanol, diethylaminoethanol, monoethylaminoethanol, their propanol and butanol counterparts, derivatives acylated with organic acids, and mixtures thereof.

12. A method according to claim 11 wherein the aminoalcohol ingredient is dimethylaminoethanol.

* * * * *